(12) United States Patent
Moneymaker et al.

(10) Patent No.: US 7,727,546 B2
(45) Date of Patent: *Jun. 1, 2010

(54) NUTRIENT SYSTEM FOR INDIVIDUALIZED RESPONSIVE DOSING REGIMENS

(75) Inventors: Ricky Dean Moneymaker, Stuarts Draft, VA (US); Larry Scott Klesman, Lake Forest, IL (US); Jon Scott Theus, Gurnee, IL (US)

(73) Assignee: Micro Nutrient, LLC, Lincolnshire, IL (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/483,208

(22) Filed: Jul. 7, 2006

(65) Prior Publication Data

US 2006/0269619 A1 Nov. 30, 2006

Related U.S. Application Data

(63) Continuation of application No. 10/868,149, filed on Jun. 15, 2004, now abandoned.

(60) Provisional application No. 60/561,097, filed on Apr. 8, 2004.

(51) Int. Cl.
*A61F 13/00* (2006.01)
(52) U.S. Cl. ..................... 424/435; 424/439
(58) Field of Classification Search ............... None
See application file for complete search history.

(56) References Cited

U.S. PATENT DOCUMENTS

| | | | | |
|---|---|---|---|---|
| 4,005,196 | A * | 1/1977 | Jandacek et al. | 514/23 |
| 5,456,677 | A * | 10/1995 | Spector | 604/290 |
| 5,770,215 | A * | 6/1998 | Moshyedi | 424/440 |
| 6,030,650 | A | 2/2000 | Kamarei | |
| 6,048,846 | A * | 4/2000 | Cochran | 514/168 |
| 6,054,477 | A | 4/2000 | Harris | |
| 6,207,203 | B1 | 3/2001 | Atkinson | |
| 6,361,800 | B1 * | 3/2002 | Cooper et al. | 424/630 |
| 6,703,371 | B1 * | 3/2004 | Wiss | 514/23 |
| 7,078,016 | B2 * | 7/2006 | Rabinowitz | 424/45 |
| 2001/0036464 | A1 | 11/2001 | Christensen | |
| 2003/0099753 | A1 * | 5/2003 | Yang | 426/599 |
| 2003/0148992 | A1 * | 8/2003 | Block et al. | 514/52 |
| 2003/0194431 | A1 | 10/2003 | Miller | |
| 2004/0001817 | A1 * | 1/2004 | Giampapa | 424/94.1 |
| 2004/0001874 | A1 | 1/2004 | Davidson | |
| 2004/0043134 | A1 * | 3/2004 | Corriveau et al. | 426/658 |
| 2004/0120991 | A1 * | 6/2004 | Gardner et al. | 424/443 |
| 2004/0191377 | A1 | 9/2004 | Malleshi et al. | |

FOREIGN PATENT DOCUMENTS

| | | | |
|---|---|---|---|
| EP | 0390435 A | | 10/1990 |
| GB | 1420883 A | | 1/1976 |
| WO | WO2004/000297 A1 | | 12/2003 |
| WO | WO2004086881 | | 10/2004 |

OTHER PUBLICATIONS

Davenas et al, Nature, vol. 333, Jun. 30, 1988, pp. 816-818.*
Wikipedia p. 1-7, search pyridoxine and pantothenic "http://en.wikipedia.org/wiki/Pyridoxine" and "http://en.wikipedia.org/wiki/Pantothenic_acid".*
Shrimpton, Derek; "RDAs-what do they really mean", The Pharmaceutical Journal, vol. 268, Mar. 16, 2002.*
http://en.wikipedia.org/wiki/Soybean (p. 1).*
http://en.wikipedia.org/wiki/Whey_protein (p. 1).*
Office Action Summary mailed Sep. 24, 2007 for U.S. Appl. No. 11/080,790, filed Mar. 15, 2005.
Office Action Summary mailed Jan. 15, 2008 for U.S. Appl. No. 11/080,790, filed Mar. 15, 2005.
Office Action Summary mailed May 12, 2008 for U.S. Appl. No. 11/080,790, filed Mar. 15, 2005.
Office Action Summary mailed Aug. 6, 2008 for U.S. Appl. No. 11/080,790, filed Mar. 15, 2005.
Office Action Summary mailed Mar. 16, 2009 for U.S. Appl. No. 11/080,790, filed Mar. 15, 2005.
"Dietary Reference Intakes for Water, Potassium, Sodium, Chloride, and Sulfate", www.nap.edu. Copyright 2004 by The National Academies.
Notification of the First Office Action for Chinese Patent Application No. 200580016730X issued Dec. 5, 2008.
Notification Concerning Transmittal of International Preliminary Report on Patentability mailed Oct. 19, 2006 for International Application No. PCT/US2005/008599.
Written Opinion of the International Searching Authority for International Application No. PCT/US2005/008599 received Aug. 11, 2005.
Notification of Transmittal of the International Search Report & the Written Opinion of the International Searching Authority dated Aug. 16, 2005 for International Application No. PCT/US2005/008599.
PCT International Search Report for PCT/US2005/008599 dated Aug. 16, 2005.
Communication from the European Patent Office dated Dec. 20, 2007 for Application No. 05 730 880.0-2108.

(Continued)

*Primary Examiner*—Robert A Wax
*Assistant Examiner*—Bethany Barham
(74) *Attorney, Agent, or Firm*—McAndrews Held & Malloy, Ltd.

(57) ABSTRACT

Individualized responsive dosing dietary supplement systems, compositions, methods of dosing, and processes of producing the same, which allow a consumer to generate individualistic biological responses/effects. More specifically, a dietary supplement system for generating individualized biological conditions/responses which utilizes ultra-low dosage amounts of vitamins, minerals, amino acids, co-enzymes, and/or other nutrients in a bio-active delivery system which preferably avoids first pass metabolism, such that an individual may take multiple doses of the same or different dietary supplement based on varying desired biological response within each 24 hour period is also disclosed.

1 Claim, No Drawings

OTHER PUBLICATIONS

International Search Report for PCT/US04/19243 dated Jun. 7, 2005.
Written Opinion of the International Searching Authority for PCT/US04/19243 dated Jun. 7, 2005.
Interview Summary dated Jun. 18, 2008 for U.S. Appl. No. 11/080,790, filed Mar. 15, 2008.

* cited by examiner

NUTRIENT SYSTEM FOR INDIVIDUALIZED RESPONSIVE DOSING REGIMENS

RELATED APPLICATIONS

This application is a continuation of U.S. patent application Ser. No. 10/868,149, filed Jun. 15, 2004, now abandoned, which claims benefit of U.S. Provisional Patent Application Ser. No. 60/561,097, filed on Apr. 8, 2004, now abandoned.

FIELD OF THE INVENTION

The present technology relates generally to individualized responsive dosing dietary supplement systems, compositions, methods of treatment, and processes of producing the same, which allow a consumer to target identifiable, individualistic biological conditions or responses. More specifically, the present technology relates to a dietary supplement system for targeting individualized biological conditions or responses which utilizes ultra-low dosage amounts of vitamins, minerals, amino acids, co-enzymes, stimulants, and/or similar ingredients in a highly bio-active delivery system, such that an individual may take multiple doses of the same or different dietary supplement mixture based on varying biological need or desired response within each 24 hour period.

BACKGROUND

Vitamins, minerals, amino acids, and co-enzymes are compounds required by an animal or human body in small amounts for metabolism, biophysiological repair, to protect health, and for proper growth and cellular reproduction. These compounds also assist in the formation of hormones, blood cells, nervous-system chemicals, and genetic material. Vitamins, minerals, amino acids, and co-enzymes are often referred to as nutrients, defined herein as a substance or ingredient which may be found in food which imparts a medicinal or health benefit. The various nutrient compounds are not chemically related, and most differ in their physiological actions. They generally act as catalysts, combining with proteins to create metabolically active enzymes that in turn produce hundreds of important chemical reactions throughout the body. Without nutrients, many of these reactions would slow down or cease. The intricate ways in which nutrients act on the body, however, are still far from clear. The Food and Nutrition Board of the National Research Council replaced and expanded the Recommended Dietary Allowances (RDAs) with Dietary Reference Intakes (DRIs) to provide recommended vitamin, mineral, or other nutrient intakes for use in a variety of settings for humans. The DRIs are actually a set of four reference values: Estimated Average Requirements (EAR), Recommended Dietary Allowances (RDA), Adequate Intakes (AI), and Tolerable Upper Intake Levels (UL). These values serve as recommended dosage levels for vitamins, minerals, or other nutrients. Currently there are no DRI's for intake of caffeine and other stimulants, or for L-glutamine or L-arginine. However, the U.S. National Library of Medicine and the National Institute of Health recommend, for example, that for caffeine, no more than 200 milligrams is taken every three or four hours, and that an adult should not take more than 1600 mg in twenty-four hours. Additionally, L-arginine is typically provided in dietary supplements in dosages of about 100 milligrams, and L-glutamine in dosages of about 500 milligrams, pursuant to the FDA.

Dietary supplements are generally nutrient mixtures commonly taken in single mega-dose dosage forms which contain vitamin, mineral and other nutrient doses equal to or over the Recommended Dietary Allowances (RDA) values. Although mega-dose regimens are a common practice for the prevention of disease, there is a great deal of debate in the literature regarding the efficacy of such regimens. Moreover, consuming large doses of vitamins, minerals, or other nutrients, in the absence of some deficiency or without proper medical supervision, may cause harmful toxic effects and/or result in hypervitaminosis.

Additionally, a consumer usually has little choice in choosing the variety of ingredients, dosage levels, or dosing regimens of a conventional dietary supplement, such as a standard vitamin tablet. Conventional dietary supplements may be effective for a general purpose, but usually provide an excess of vitamins, minerals, stimulants, or other compounds which a consumer does not desire, or those supplements may not adequately target an individual's specific dietary need or desired biological response. Additionally, conventional dosage forms of dietary supplements only allow a consumer to take one or two doses per 24 hour period. As a result, conventional dietary supplements fail to recognize that the physiological state and resultant nutrient requirements of any single individual can depend upon and fluctuate based upon a number of different biophysical variables during the course of each day or dosing regimen. For example, individual variations in diet, and the amount and intensity of physical activity, provide physical and chemical stimuli that stress various systems of the body to differing degrees from one person to the next and for each of those individuals on any given day. Thus, standard "one size fits all" mega-dose dosage forms/regimens are not amenable to empirical dosage adjustment to achieve an individualized biophysiological objective or response.

Another drawback with most conventional dietary supplements is that they suffer from poor degrees and/or rates at which the various nutrients are absorbed into the systemic circulation of the body and made available for biophysiological activity (e.g., "bioavailability"). These degrees or rates of bioavailability typically depend upon the dose, dosage form, and method of administration.

One particular barrier to efficient nutrient bioavailability is "first-pass metabolism", which is defined herein to mean a process in which the nutrient compound(s) are modified, activated, or inactivated before they enter the systemic circulation, or are left unchanged and excreted. Alternatively, it may be defined as the intestinal and hepatic degradation or alteration of a drug or substance taken by mouth, after absorption, removing some of the active substance from the blood before it enters the general circulation.

For example, it is believed that one significant drawback to "mega-dosing" of vitamins and minerals is that increased dosages may not be adequately absorbed into the body, or may actually decrease absorption. Thus, available transport mechanisms may become saturated and unable to absorb excess dosage. Additionally, a drawback to vitamin or mineral delivery via a conventional tablet or capsule is that differences in luminal pH along the gastrointestinal tract lining, surface area per luminal volume, blood perfusion, presence of bile and mucus, and the nature of epithelial membranes may prevent efficient absorption, activation, and the like of a nutrient, thereby decreasing its bioavailability.

To compensate for first pass metabolism effects, some previous efforts have been directed to enterically coated tablet or capsule dosage forms which pass through the stomach unaltered to disintegrate in the lower intestines. However, aside from a delayed biophysiologic response as gastric emptying becomes rate-limiting, gastric irritability, and potential allergic reactions from the ingestion of such coating materials occurs, and these enterically coated delayed release dosage forms dissolve and are absorbed within a narrow time frame. As a result, the body typically excretes the non-absorbed vitamins or minerals.

Additional previous attempts have been directed to continuous or gradual release dosage forms. U.S. Pat. No. 4,882,167, to Jang, discloses dry direct compressed products for controlled release of actives including vitamins or minerals. However, the compositions and methods of the Jang patent do not provide for ultra-low dosage amounts of vitamins or minerals, dosing flexibility, or systems, compositions, or methods for individualized responsive dosing based on a desired biological response.

WO 99/17753 discloses rapidly dissolving films for delivery of drugs to be adsorbed in the digestive tract. U.S. Pat. No. 6,596,298, to Leung, discloses consumable oral care films which may optionally contain active amounts of pharmaceutical drugs. However, these patents do not utilize vitamins or minerals, and more specifically, ultra-low dosage amounts of nutrients which would operate to provide flexibility for individualized dosing. Moreover, these products or processes do not provide a system or selection for varying the type or level of dosage depending on a biological response desired.

Therefore, there is presently a need for an efficient process for producing a nutrient dosage and delivery system that is capable of individualized biological response dosing (i.e., dosing based upon empirical analysis and adjustment), which is available in a suitable dosage form, and preferably is efficiently absorbed and made bioavailable to animal or human tissue. Additionally, there is presently a need for a treatment method for managing finely tuned biological needs and responses which utilizes ultra low dosage amounts, substantially avoids first pass metabolism, and allows for varied dosage/dosing regimens within each dosing period (e.g., 24 hours, 6 hours, 1 hour).

SUMMARY OF THE INVENTION

Embodiments of the presently described technology provide one or more of the following advantageous features and/or objects:

(1) Efficient production of varied and separate nutrient composition series that are configured to generate discrete types of biological responses in the body;

(2) Efficient production of a single series of nutrient compositions containing varying levels or ranges of ingredients to generate varying levels or ranges of biological response in an animal or human body;

(3) Efficient rate of absorption into an animal or human body to improve bioavailability, biokinetics, and biodelivery;

(4) Efficient bioavailability of multiple vitamins, minerals, amino acids, co-enzymes, and/or other nutrient compounds in concert;

(5) Avoidance of first pass metabolism effects, transport mechanism saturation, or excretion of significant amounts of a nutrient composition;

(6) A biological response equivalent dosing unit that does not approach RDA or UL amounts, but is still effective in enhancing the overall well being of an individual and generating a biological response;

(7) The ability to take multiple doses of a single finely tuned nutrient composition as need varies within each week, day, and/or hour; and (8) The ability to take multiple doses of different finely tuned nutrient compositions as different needs develop during each week, day, and/or hour.

Other objects and advantages of the presently disclosed technology will become apparent to those skilled in the art who have the benefit of this specification and the prior art.

In preferred embodiments of the presently described technology, there are provided processes for producing an individualized responsive dosing nutrient system, the resultant products of such processes, compositions for use in an individualized responsive dosing nutrient system, and a method for generating a biological response utilizing the system.

The process for producing an individualized responsive dosing nutrient system preferably first comprises a starting water source which preferably contains beneficial, but ultra low dosage levels of at least one nitrate, at least one nitrite, and at least one mineral. A base mixture is then added containing at least two vitamins and/or minerals, which is selected from a group of two or more base compositions configured to generate one or more pre-determined biological responses. The base mixture is preferably selected based on a desired biological response for the finished dietary supplement composition. A pre-mix composition, which is preferably of a constant compositional make-up during different runs of the process, is then added or, alternatively, is added as part of the base mixture.

Optionally, the mixture comprising the water, base mixture, and pre-mix, may then be further diluted based on a pre-determined dilution factor, to vary the ultimate dosage levels in the finished nutrient composition. Alternatively, the amount of base mixture may be varied during processing based on a pre-determined multiplier.

Then, the mixture containing water, base mixture, and pre-mix, and optionally further water, is configured into or onto a delivery system (such as, but not limited to an oral film) which substantially avoids first-pass metabolism, to form a finished single nutrient composition. Additionally, it is preferable that the dosage level of any vitamin, mineral, amino acid, or co-enzyme contained in the finished nutrient compositions of the presently described technology be less than 25% of the RDA or UL for such vitamin, mineral, amino acid, co-enzyme, or other nutrient. More preferably, the dosage levels are less than 10%, 1%, or 0.1% of RDA or UL for each nutrient. In the most preferred instances, the dosage levels are less than 0.001% or less than 0.0001% of RDA or UL. Preferably, however, the dosage levels are at least $1 \times 10^{-7}\%$ of RDA or UL. An illustrative formulation for a finished single dose (5 drops) of a final formulation in a liquid delivery system of the present technology is given in Example 17, below.

Finally, the foregoing process steps may be repeated one or more times, more preferably five or more times, and most preferably, ten or more times, and either a different base mixture is selected, or a different dilution or base multiplication factor is selected, to produce a system/series of nutrient compositions capable of being utilized for individualized biological responsive dosing.

Other embodiments of the presently described technology set forth below illustrate the resultant products of such a process(es) for the production of an individualized responsive dosing dietary supplement system, as well as specific base mixtures and set pre-mix compositions for use in such process and system(s).

Additionally, there is presently described a method for individualized responsive dosing to generate a biological response, comprising the steps of providing a selection of two or more nutrient formulations in delivery systems which substantially avoid first pass metabolism and which provide two or more vitamins, minerals, amino acids, co-enzyme, or other nutrient in amounts preferably less than 10% or 1% of RDA or UL, more preferably less than 0.01% of RDA or UL, and most preferably less than 0.0001% of RDA or UL and a water source comprising at least one mineral, nitrate, nitrite, and/or other nutrients in amounts preferably less than 0.001% of RDA or UL. Preferably, however, the dosage levels are at least $1 \times 10^{\wedge}7\%$ of RDA or UL. The two or more nutrient compositions are preferably separately configured to generate one or more pre-determined biological responses, including, but not limited to: stress-relief, cellular metabolism, energy conservation, energy utilization, energy enhancement, enhanced memory, enhanced cognitive function, calmness, awareness, stimulation of the hypothalamic-pituitary-thyroid axis, fatigue relief, enhanced immune response, antioxidation, liver detoxification, and alcohol metabolism.

Additional embodiments are disclosed in the detailed description provided below. While the presently described technology will be provided in connection with one or more preferred embodiments, it will be understood by those skilled in the art that the presently described technology is not limited to those embodiments. To the contrary, the presently described technology includes all alternatives, modifications, and equivalents as may be included within the spirit and scope of the appended claims.

DETAILED DESCRIPTION OF THE INVENTION

It has been unexpectedly and surprisingly discovered that the dose of a vitamin, mineral, or other nutritional supplement ingredient, when adapted for delivery via a system that substantially avoids first pass metabolism, may be significantly reduced while still producing a desired beneficial effect/biological response. As a result, the ingredients of a dietary supplement may be provided at substantially lower levels (i.e. ultra-low levels) than those recommended by the government as a raw material standard (RDA, UL, UDA, etc.). Furthermore, it has been surprisingly discovered that such ultra-low dosage levels and bioactive delivery systems allow dietary supplement compounds to be repeatedly and flexibly administered to an animal or human for the enhancement and augmentation of those biological functions known to be influenced by any of the individual components. These biological functions include without limitation those processes associated with: cellular metabolism including nucleic acid and amino acid metabolism; energy metabolism including energy conversion, utilization, and enhancement; mental acuity including memory and cognitive function; the nervous system including neuromuscular transmission and propagation; hormone responses including stimulation of the hypothalamic-pituitary-thyroid axis; management of peripheral and central fatigue including the enhancement of antioxidant defense systems; the mitigation of episodic and/or chronic stress; and detoxification by the liver including increased alcohol metabolism.

Specifically, it is believed that due to the ultra-low dosage levels utilized in the present technology, a specific composition may be taken by an individual multiple times within each dosing period (e.g., within each 24 hour, 6 hour, or 1 hour period). Alternatively, an individual may take multiple, different compositions within a dosing period to generate varied biological responses or effects. Thus, the presently described technology may be utilized in a system which allows an individual to biologically configure their dietary supplement intake throughout a dosing period or multiple dosing periods, based on their individual needs.

Accordingly, the presently described technology describes processes for producing an individualized biologically responsive dosing dietary supplement system, the resulting products of such processes, compositions for use in an individualized responsive dosing system, and a method of treatment for generating a biological response utilizing the individualized responsive dosing system.

In one embodiment of the present technology, there is provided a process for producing an individualized biologically responsive dosing system that as a dietary supplement, first comprises a starting water source which preferably contains beneficial, but ultra-low dosages of at least one nitrate, at least one nitrite, at least one mineral, and/or other nutrients. A base mixture which comprises at least two vitamins, minerals, or other nutrients, more preferably at least three vitamins or minerals, and most preferably at least five such nutrients is added to the water. The base mixture is preferably selected from a group of two or more base mixtures configured to generate one or more pre-determined biological effects. More preferably, the base mixture is selected from a group of five or more base mixtures, and most preferably, a group of 10 or more. The base mixture is preferably selected based on a desired biological response for the finished nutrient formulation. Then, a pre-mix composition, which preferably comprises constant percentage ratios of certain vitamins, minerals, amino acids, co-enzymes, or other nutrients during processing, is either added separately or, more preferably, is included as part of the base mixture during preparation to a final, finished nutrient formulation. The pre-mix, discussed in detail below, preferably contains at least three or more, and more preferably, at least five or more, different vitamins, minerals, amino acids, co-enzymes, and/or other nutrients.

Optionally, as an alternative embodiment, an intermediate mixture comprising the water, base mixture, and pre-mix may be further diluted based on a preferably pre-determined dilution factor, to vary the ultimate dosages of the nutrients in the final formulation. This enables a manufacturer to easily create a range of dosage formulations. Alternatively, the amount of base mixture may be varied during processing based on a multiplier. Both the multiplier or dilution factor are experimentally determined. Preferably, the multiplier ranges from 20 to 40. Although not wanting to be bound by any particular theory regarding the multiplier and/or dilution factor, it is believed that because a water source is used, preferably from a known, specific source, a pre-mix, a selection of base mixtures, and a set procedure for making the strips or liquid, then a multiplier or dilution factor may be utilized to produce a series of related nutrient formulations, which can elicit a range of certain biological effects/responses in an animal or human body (i.e. stimulation, arousal, drowsiness, energy, etc.) within that single series.

After any optional dilution step, the mixture containing water, base mixture, and pre-mix is configured into a final, finished formulation for delivery to an animal or human which substantially avoids first-pass metabolism. Suitable and preferred delivery systems are discussed in detail below. Again, while not limited to any one theory, it is believed that by utilizing a delivery system which bypasses first-pass metabolism, the vitamins, minerals, amino acids, co-enzymes, and/or other nutrients are more readily made available in the body (e.g., increased "bioavailability"). It is also believed that the avoidance of transport mechanism saturation and excretion of excess ingredients permits the use of much lower amounts/dosages of components than in conventional dietary supplements, while still providing beneficial biological effects/responses. Moreover, utilizing lower amounts/dosages of ingredients allows for multiple uses of a single or related formulation, or use of another type of formulation, as an individual's biological need or desired response varies throughout each dosing period (e.g., each 24 hours, 6 hours, or 1 hour). Furthermore, it is believed that such individualized responsive dosing is possible in part because the dosage level of any vitamin, mineral, amino acid, or co-enzyme contained in the final formulation (i.e. the final oral strip, liquid drops, capsules, troches, lozenges, etc.) of the instant process are less than about 25% of the RDA or UL of such vitamin, mineral, amino acid, or co-enzyme. More preferably, the dosage levels are less than about 10% or less than 1% of the RDA or UL, and most preferably, less than about 0.10% or about 0.01% of the RDA or UL. Some preferred embodiments have dosage levels of less than about 0.001% of the RDA or UL.

When referred to in the instant technology, the UL is defined as the maximum level of daily intake of any vitamin, mineral, amino acid, co-enzyme, or other composition that is likely to pose no risk of adverse effects, and the RDA is defined as the Recommended Dietary Allowance. Both values are preferably those published by the Food and Nutrition Board of the National Research Council, for Males 19-30 years old. See Example 16: RDA/UL for Some Nutrients. It will be understood, however, that the present invention is not limited to those vitamins, minerals, amino acids, co-enzymes, or other compositions for which RDA values or UL values have been established by a governing body, and may encompass any nutrient composition.

Furthermore, based on known amounts of vitamin, mineral, amino acid, or co-enzyme amounts in a pre-mix or base composition, a known dilution factor or multiplication factor, and further based on a selected, constant process for producing a final formulation, the final dosage amounts of any components in the final formulation (i.e. the final oral strip, liquid drops, capsules, troches, lozenges, etc.), can be calculated.

After a single form of the nutrient formulation is produced, the foregoing process steps may be repeated one or more times, preferably five or more times, and most preferably, ten or more times to produce different doses of a formulation for a particular "series" of that formulation, or different types of formulations for different series. Either a different base mixture is selected, or a different dilution or multiplication factor is selected, to produce a system of nutrient compositions capable of being utilized to generate biological responses.

For example, a manufacturer may efficiently create a number of different series, such as illustrative Series S, Series T, Series U, Series V, Series K, Series L, Series M, Series N, Series X, and Series W, by utilizing different base mixtures. Examples 4 through 13 describe preferred base compositions for creation of the foregoing series. Each series may generate a desired and distinct biological effect or responses, or may overlap slightly in degree of the same response. Within each series, a manufacturer may utilize differing dilution or multiplication factors to efficiently create a gradient of biological responses (i.e. sleep (low energy) to awake and active high energy). Examples 3 and 15 gives a examples of a gradient of dilution factors and corresponding biological effects/responses observed within a given series. (Series S).

Below is a detailed description of each of the preferred steps and components in the presently described technology for producing an individualized responsive dosing dietary supplement system. The compositions of the present technology can include any of the water-soluble and/or fat-soluble vitamins, a coenzyme such as $Q_{10}$, essential and/or non-essential amino acids, and minerals including without limitation calcium, phosphorus, magnesium, sodium, potassium, chloride, chromium, copper, fluoride, iodine, iron, manganese, molybdenum, selenium and zinc. The presently described technology can also include other ingredients, for example, nitrate, nitrite, folic acid, and stimulants such as caffeine. It is also contemplated that the compositions of the present technology may further include pharmaceutical compositions.

Water

The water can vary from source to source, but preferably contains at least one nitrate, at least one mineral, and at least one nitrite. Most preferably, the presently described technology utilizes water from an Appalachia water source, preferably a water source from the Eastern slope of the Shenandoah Valley. Different water sources would require empirical analysis of its constituents to ensure that the dosage amounts are consistent with spirit of the presently described technology. For example, the base composition multiplier could be changed in order to obtain an adjusted base with a preferred compositional make-up in light of a different water source.

The water is preferably filtered to purify and refine it from the certain, selected water-source. The filter is preferably a commercially available filter having a pore size of about 0.1 micron. An example of components that the water can include, and tolerances for the amounts of those components, is set forth below:

Nitrate 0-0.10 mg/L+25%
Nitrite 0-0.01 mg/L+25%
Calcium 0-12.4 mg/L+25%
Chromium 0-0.001 mg/L+25%
Magnesium 0-5.8 mg/L+25%
Manganese 0-0.001 mg/L+25%
Potassium 0-1.4 mg/L+25%
Sodium 0-1.6 mg/L+25%

Any of these preferred components of the water may range from 0 to +25%. The pH of the water can range from about 5 to about 7.5. Preferably, the pH of the water is about 7.50 at 25 degrees Celsius.

Base Mixture

Preferably, a selection of base mixture is provided so that various base mixtures may be utilized to create different series of final formulations. It is also preferable that each base mixture is configured to generate a desired biological response. Either completely different or overlapping biological responses may be generated by different base mixtures. Additionally, each of the base mixtures may already contain a pre-mix with constant compositional make up. The pre-mix need not be identified as such, but may merely contain at least two or more vitamins, mineral, amino acids, or other nutrient which can remain constant (i.e. in relative proportion to one another) within each base mixture.

The components of the base mixture preferably comprise at least two of the following: magnesium chloride, sodium chloride, potassium chloride, calcium chloride, ascorbic acid, caffeine, niacin, potassium benzoate, chromium picolinate, chromium, polynicolinate, coenzyme Q10, L-glutamine, potassium sorbate, calcium ascorbate, sodium nitrite, L-arginine, or sodium ascorbate. More preferably, the base mixture comprises at least five of the foregoing.

Illustrative examples of base mixtures of the present technology are embodied in Tables 4 through 13 and have been designated as series S, T, U, V, K, L, M, N, X and W. Those examples illustrate the preferred makeup in grams of the individual ingredients/components of exemplar base compositions, including the amount of vitamin premix used and the amount of any additional components admixed with the vitamin premix. For example, Table 4 illustrates that the base composition for the S series comprises 0.02500 grams of vitamin premix admixed with additional components, including for example 0.06000 grams of magnesium chloride. Also shown is the adjustment of each component of the base composition by application of a dilution or multiplication factor to arrive at the adjusted base composition. For illustrative purposes, the multiplier is based upon the dissolution of the selected components in a final volume of 1 gallon of profiled water.

Any base composition multiplier may be experimentally determined in regards to a desired biological effect/response, and is, for illustrative purposes, established relative to that water characterized in Example 2. A multiplication factor is preferably empirically determined so as to compensate for variables. The variables that are taken into consideration can include without limitation: any additional ingredients/components coming from selected water sources used for dissolution; any processing required to arrive a final dosage form; and/or any adjustments required to achieve a desired biological response/effect. The multiplier is empirically derived and can range from a factor of about 20 to about 40. This multiplier is utilized to create a final adjusted base composition, which will achieve the adequate amount of each component per base composition, which can then be further formulated into a specific dosage form and chosen for application based on desired biological effects/responses on any living system, human or otherwise.

For further illustrative purposes, each exemplar series S, T, U, V, K, L, M, N, X and W may be further divided into sub-series based on varying dosage amounts. For example, the S-series may contain subs-series S-1 through S-10 compositional products, which vary in their solids content with S-1 having less solids than S-10 based upon the dilution rate of the S series adjusted base composition. See Example 15. The grouping of compositional products, produced by dilution in the selected water of each of the representative adjusted base composition mixtures, is illustrated in Tables 14-22 for each additional exemplar series T, U, V, K, L, M, N, X and W.

Pre-Mix

The general pre-mix formulation is preferably comprised of pharmaceutical grade vitamins, minerals, amino acids and/or coenzymes. Each ingredient is preferably on the United States Food and Drug Administration's Generally Recognized As Safe (GRAS) list. An illustrative example of a standard premix composition is shown in Example 1 and includes vitamins A, B1, B2, B3, B6, B12, C, D3, E and H, in admixture with folic acid, copper, iron, potassium iodide, calcium carbonate, and zinc. A further embodiment of the present technology includes base compositions containing the vitamin premix composition in addition to any further components/ingredients added to the vitamin premix composition. By way of example, additional components/ingredients added to the vitamin premix to form a base composition may include without limitation magnesium chloride, sodium chloride, potassium chloride, calcium chloride, ascorbic acid, caffeine, niacin, potassium benzoate, chromium picolinate, chromium polynicolinate, coenzyme Q10, L-glutamine, and potassium sorbate, sodium ascorbate, potassium carbonate, calcium ascorbate, calcium carbonate, L-arginine, sodium nitrite, and combinations and derivatives thereof.

In the preferred embodiments of the presently described technology, the compositional make-up of the pre-mix formulation does not vary during processing, or in separate types or series of finished product. The pre-mix dosage amounts, however, are preferably adjusted through dilution or multiplication of the base mixture.

Delivery System

For the present technology, any dosage form can be utilized. Those dosage forms can include, for example, an oral film, tablet, pill, liquid, capsule, lozenge, troche, suppository, transdermal patch, nasal sprays, dragus, slurry, suspension, or emulsion. For this particular technology, dosage administration routes are preferably those that by-pass first pass metabolism such as buccal, nasal, transdermal, intradermal, intramuscular, intravenous and certain rectal routes. This is due to the present technology believing to have enhanced efficacy by circumventing dosage administration routes which would undergo first pass metabolism (oral, in particular).

Compositions of the present technology can be preferably formulated for either parenteral or enteric absorption. Parenteral absorption generally comprises absorption by way other than the gastrointestinal track and without significant first pass metabolism. By way of example and without limitation, parenteral absorption can be pre-gastric, topical, optical, intravenous, and/or by oral or nasal inhalation. Pre-gastric absorption as used herein comprises absorption of an ingredient from that part of the alimentary canal prior to the stomach, and includes without limitation buccal, sublingual, oropharyngeal and esophageal absorption. It is envisaged that such pre-gastric absorption will occur primarily across the mucous membranes in the mouth, pharynx and oesophagus. The present invention, however, is not limited to any one method of delivery, and envisions delivery via any tissue with an adequate rate of absorption, which avoids first pass metabolism.

It is preferred that the composition of the present invention is formulated to promote absorption of ingredients/components of the final formulation through the buccal, sublingual, pharyngeal and/or esophageal mucous membranes. Without being bound by a particular theory, it is believed that pre-gastric absorption will occur primarily across the mucous membranes in the mouth or oral cavity, pharynx and esophagus. The oral mucosa has a thin epithelium and a rich vascularity that favors absorption. Blood capillaries are extremely close to the surface in these areas and readily absorb the ingredients into the blood stream. The flow is from this area of the mouth to the Carotid Artery and it is envisaged that distribution to the brain and the rest of the body will be rapid, thereby resulting in greatly enhanced efficacy and/or rates of response.

It is also envisaged that the compositions of the present invention can be formulated to be fast-dispersing and bioadherent for application to the surface of another product intended for enteric absorption. Accordingly, any of the compositions of the present invention upon rapid dissolution from the surface of said other product can be retained in the oral cavity so as to facilitate pre-gastric absorption, while the balance of said other product moves further into the GI tract to undergo enteric absorption.

It is also believed that ingredients absorbed by pre-gastric absorption will pass straight into the systemic circulatory system and thereby avoid the gastrointestinal track and first pass metabolism in the liver. Accordingly, bioavailability of an active ingredient delivered in this way may also be increased. Additionally, the bioavailability of a number of vitamins, minerals, amino acids, co-enzymes, and/or other nutrients in concert can also be increased. It is desired that the dose of an ingredient may be minimized, while still producing the desired beneficial effects, with close to zero order kinetics (immediate efficacy) thereby decreasing the required dose. These concentrations may vary and will be selected primarily on the desired biological response and dosage form selected.

U.S. Pat. Nos. 6,596,298; 6,569,463; 5,948,430; 6,592,887; 5,629,003; 6,419,903; and 6,316,029 disclose various delivery systems which may be utilized in the present technology.

One particularly preferred method of delivery, although not limited to any one method, is a consumable oral strip. The dosage form can include by way of example and without limitation, a starch, pectin, and/or cellulose based strip or film that adheres to and dissolves in a mouth of a consumer. A strip formulation is made utilizing conventional film formulation processing and technology. The preferred film formulation is a starch-based film formulation or matrix. Other film formulation matrixes can be utilized such as pectin and other film bases (cellophane tape).

Based on selected amounts of vitamin, mineral, amino acid, co-enzyme, and/or other nutrients in a selected pre-mix or base composition, a selected dilution factor or multiplication factor, and further based on a selected, constant process for producing a final formulation, a final dosage amount of components/ingredients in a finished oral strip may be determined. The dosage level will be determined therefore, by the number of strips made per gallon of the mixture comprising water, base mixture, and pre-mix. Preferably, this rate of strips per gallon of mixture is a constant during processing, such that variation in the finished product is achieved through the afore-mentioned multiplication and dilution factors. Optionally, the rate of strips per gallon may also be adjusted to vary finished nutrient formulation properties. A conventional oral strip processing method is disclosed in U.S. Pat. No. 6,596,298 to Leung ("the Leung patent").

In preferred methods of strip formulation, approximately 2020 grams of the mixture comprising water, base mixture, and pre-mix (regardless of the dilution factor and/or multiplication factor) is used per 454 grams of strip matrix. Additionally, preferred oral strips have dimensions of approximately 35.356 $mm^3$ with a tolerance of +/−5%. As one illustrative example, in preferred strip formulation processing, when utilizing a K-16 formulation, approximately 19,500 strips may be made from approximately one gallon of K-16.

Individualized Responsive Dosing

Additional embodiments of the present technology include individualized responsive dosing methods, wherein an individual may select from different series or types of nutrient components within a series based on varying need or desired biological response needed throughout each 24 hour period (or in some embodiments, each 6 hour or 1 hour period). The preferred method of dosing provides a selection of three or more nutrient formulations in delivery systems which substantially avoid first pass metabolism, and each member of the selected nutrient formulations comprises: (a) at least five or more vitamins, minerals, amino acids, co-enzyme, or other nutrients in amounts no greater than about 25% of the Recommended Daily Allowance (RDA) or Upper Limit (UL); (b) water containing at least one mineral, nitrate, and nitrite, each in an amount less than about 25% of the RDA or UL for that component; and (c) optionally, a stimulant. Furthermore, each of the three or more nutrient formulations is separately configured to generate a specific, pre-determined biological response/effect.

The different formulations of the present technology may be configured to generate the following pre-determined biological responses: cellular metabolism including nucleic acid and amino acid metabolism; energy metabolism, including energy conversion and utilization; mental acuity, including memory and cognitive function; nerve signaling including neuromuscular transmission and propagation; hormone signaling including stimulation of the hypothalamic-pituitary-thyroid axis; management of peripheral and central fatigue, including the enhancement of antioxidant defense systems; the mitigation of episodic and/or chronic stress; and detoxification by the liver including increased alcohol metabolism.

Preferably, each formulated series has a different biological effect/response which can be graded within the series. In other words, a series such as exemplary Series S may be anecdotally shown to produce varying levels of energy or relaxation per composition/formulation within the series. Thus, for illustration purposes, the gradient of Example 15 may be observed.

Although not wanting to be bound be any particular theory, it is believed that a series such as the exemplary S series may enhance biochemical signal processing within cellular tissues to cause a gradient of energy levels observed which are dependent upon the concentration (i.e., solids content) of the composition within the series utilized (i.e., S-1 biological effects v. S-10 biological effects). It is further believed that such energy enhancement effects are due to enhanced cellular radical scavenging, oxygenation, or utilization of GABA as well as tissue responses such as vasodilation or enhanced glomerular filtration.

Additionally, as previously described, the administration of these formulations to the body in a delivery system which preferably avoids first pass metabolism increases bioavailability of the formulations to the body, which in turn enhances component ingredient capacity or concentrations at a cellular level to the tissues, which in turn again with increased capacity improves cellular absorptive capacity of the component/ingredient leading to a biochemical signal being generated to those tissues and a biological/biochemical response produced.

Therefore, an individual may select one of the series to begin with and attempt to achieve a particular desired biological response. For example, the patient may select the S-series to achieve enhanced levels of energy or drowsiness depending upon which composition within the S-series is selected. If the patient selects an illustrative S-1 composition, then the patient could preferably take 1 strip or 1 drop of the composition at a time to try and achieve the "energy" effect desired. If the effect is not achieved, then the patient may continue with a strip by strip or drop by drop approach to try and achieve the particular biological effect desired with that particular composition of the series. This particular dosage methodology is an individualized responsive dosing or titration approach. For a liquid formulation, an individual may preferably begin with 5 drops and continue to titrate drop by drop to attempt to achieve the desired biological response/effect. For comparison purposes, 120 drops equal 1 Teaspoon.

If the composition of the series still does not provide the biological response/effect the individual desires, then the individual can select a high solids content formulation within the series such as, for example, S-2 to S-10 to try and achieve the desired effect (or change of effect, i.e., from sleep to energy) on a strip by strip or drop by drop basis again.

Finally, if the individual still does not achieve the desired biological response/effect with that particular series/formulation, then the individual may select another series and continue with the foregoing approaches again to see if the desired biological response/effect can be achieved. A different series/formulation may generate completely different biological responses/effects (i.e. calmness versus enhanced memory), or may overlap in its response/effect. For example, in illustrative examples S and K, the only differences are that S starts at a lower energy level than K where K starts at a higher energy level immediately at the K-1 sub-series. In contrast, S-1 is more suitably directed to sleep promotion. Likewise, a T-1 formulation will have a different biological effect than an S-1 formulation, although certain T Series formulations may have similar biological effects to certain S Series formulations (i.e., effect/response overlap). Yet, the same individualized responsive dosing approach is utilized.

As previously described, the overall dosing methodology above is referred to as individualized responsive dosing since the individual is dosing his or herself in a stepwise fashion to attempt to achieve the desired biochemical signal and resultant biological effect, response, or condition. Conventional vitamin regimens do not allow patients to variably and individually dose themselves based upon their biological responses and biochemical signals because conventional vitamin/mineral compositions are a one mega-dose/one dosing regimen fits all type approach which would be counter to the presently described technology's individualized responsive dosing approach.

The following examples describe some of the preferred embodiments of the present technology without limiting the technology thereto. Other embodiments include, but are not limited to, those described in the above written description, including additional or alternative components, alternative concentrations, and additional or alternative properties and uses.

EXAMPLES

Example 1

Pre-Mix Composition

| Component | Amount | | Component | Amount | |
|---|---|---|---|---|---|
| Vitamin A | 6000 | usp | Vitamin $D_3$ | 480 | usp |
| Vitamin $B_1$ | 0.00519 | mg | Vitamin E | 35 | usp |
| Vitamin $B_2$ | 0.00392 | mg | Vitamin H | 0.00045 | ug |
| Vitamin $B_3$ | 0.05 | mg | Folic Acid | 0.00048 | ug |
| Vitamin $B_6$ | 0.05 | | Copper | 0.0022 | mg |
| Vitamin $B_{12}$ | 0.000015 | ug | Iron | 0.0191 | mg |
| Vitamin C | 0.15 | mg | Potassium Iodide | 0.000165 | ug |
| Zinc | 16.1 | mg | Calcium carbonate | 0.1 | mg |

Example 2

Water Composition

| Analyte | Result | Units |
|---|---|---|
| Nitrate | <0.10 | mg/L |
| Nitrite | <0.01 | mg/L |
| Calcium | 12.4 | mg/L |
| Chromium | <0.001 | mg/L |
| Magnesium | 5.8 | mg/L |
| Manganese | <0.001 | mg/L |
| Potassium | 1.4 | mg/L |
| Sodium | 1.6 | mg/L |

Example 3

Typical Method for Optional Dilution

| Sub-series | Dilution rate to 1 gallon mixture for processing into final product |
|---|---|
| S-1 | 0.5 oz to 1 gallon |
| S-2 | 1 oz to 1 gallon |
| S-3 | 2 oz to 1 gallon |
| S-4 | 3 oz to 1 gallon |
| S-5 | 4 oz to 1 gallon |
| S-6 | 5 oz to 1 gallon |
| S-7 | 6 oz to 1 gallon |
| S-8 | 7 oz to 1 gallon |
| S-9 | 8 oz to 1 gallon |
| S-10 | 9 oz to 1 gallon |
| S-11 | 10 oz to 1 gallon |
| S-16 | 15 oz to 1 gallon |
| S-21 | 20 oz to 1 gallon |
| S-26 | 25 oz to 1 gallon |

Dilution Method for all S Series products - Mix initial proscribed amount of Base Mixture with the same quantity of profiled water. Agitate for 1 minute per dilution. Repeat until 1 gallon of finished mixture is produced. For example, 8 such steps are required for S-1. Preferably, wait about 8 hours between dilution steps.

Example 4

Base Composition for Series S

| Base Composition | Base Amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |

Example 5

Base Composition for Series T

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |

Example 6

Base Composition for Series U

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |

Example 7

Base Composition for Series V

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |

-continued

| Base Composition | Base amount (grams) | Multiplier | Adjusted Base Composition (Dissolved in 1 gallon Select Water = Adjusted Base Composition Mixture) |
|---|---|---|---|
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |

Example 8

Base Composition for Series K

| Base Composition | Base Composition (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid (ester C) | 0.50000 g | 23 | 11.5 g |
| Caffeine | 0.09500 g | 23 | 2.185 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |

Example 9

Base Composition for Series L

| Base Composition | Base Amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.09500 g | 23 | 2.185 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |

Example 10

Base Composition for Series M

| Base Composition | Base Amount (Grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium chloride | 0.09000 g | 23 | 2.07 g |
| Potassium chloride | 0.09000 g | 23 | 2.07 g |
| Calcium chloride | 0.06000 g | 23 | 1.38 g |
| Ascorbic acid (ester C) | 0.50000 g | 23 | 11.5 g |
| Caffeine | 0.09500 g | 23 | 2.185 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |

Example 11

Base Composition for Series N

| Base Composition | Base Amount (Grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.09500 g | 23 | 2.185 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.06250 g | 23 | 1.4375 g |
| L-Glutamine | 0.25000 g | 23 | 5.75 g |
| Potassium sorbate | 0.10000 g | 23 | 2.3 g |
| Sodium nitrite | 0.07250 g | 23 | 1.6675 g |

Example 12

Base Composition for Series W

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| L-Arginine | 0.25000 g | 23 | 5.75 g |
| Potassium sorbate | 0.10000 g | 23 | 2.3 g |
| Sodium nitrite | 0.07250 g | 23 | 1.6675 g |

Example 13

Base Composition for Series X

| Base Composition | Base amount (grams) | Multiplier | Adjusted Base Composition (Dissolved in 1 gallon Select Water = Adjusted Base Composition Mixture) |
|---|---|---|---|
| Magnesium chloride | 0.06000 g | 23 | 1.38 g |
| Sodium ascorbate | 0.09000 g | 23 | 2.07 g |
| Potassium carbonate | 0.09000 g | 23 | 2.07 g |
| Calcium ascorbate | 0.06000 g | 23 | 1.38 g |
| Ascorbic acid (ester C) | 0.50000 g | 23 | 11.5 g |
| Caffeine | 0.04750 g | 23 | 1.0925 g |
| Niacin | 0.01000 g | 23 | 0.23 g |
| Potassium benzoate | 0.04500 g | 23 | 1.035 g |
| Vitamin Premix | 0.02500 g | 23 | 0.575 g |
| Chromium picolinate | 0.0001870 g | 23 | 0.004301 g |
| Chromium polynicolinate | 0.0001870 g | 23 | 0.004301 g |
| Coenzyme Q10 | 0.03125 g | 23 | 0.71875 g |
| L-Glutamine | 0.25000 g | 23 | 5.75 g |
| L-Arginine | 0.25000 g | 23 | 5.75 g |
| Potassium sorbate | 0.10000 g | 23 | 2.3 g |

Example 14

Typical Oral Strip Ingredients

| Component | Results (mg/strip) |
|---|---|
| Nitrate | <0.002 |
| Nitrite | <0.0002 |
| Calcium | 0.1279 |
| Chromium | 0.000055 |
| Magnesium | 0.037 |
| Manganese | 0.00001 |
| Potassium | 0.23 |
| Sodium | 2.442 |

Example 15

Dosage Gradient Within a Series

S-1 Generates a biochemical signal for sleep (almost unconscious)

S-2 Generates a biochemical signal for relaxation

S-3 Generates a biochemical signal for calmness

S-4 Generates a biochemical signal for decreased anxiety

S-5 Generates a biochemical signal for increased mental alertness

S6-S7 Generates a biochemical signal for increased mental acuity and focus

S-8 Generates a biochemical signal for increased energy

S-9 Generates a biochemical signal for further increased energy without the sensation of a lactic acid burn S-10 Generates a biochemical signal for enhanced energy sensation.

Example 16

RDA/UL Values for Some Nutrients

| Nutrient | RDA (mg/day) | UL (mg/day) |
|---|---|---|
| Folate | 0.4 | 1 |
| Niacin | 16 | 35 |
| Pantothenic Acid | 5 | ND |
| Vitamin B2 | 1.3 | ND |
| Vitamin B1 | 1.2 | ND |
| Vitamin A | 0.9 | 3 |
| Vitamin B6 | 1.3 | 100 |
| Vitamin B12 | 2.4 | ND |
| Vitamin C | 75 | 2000 |
| Vitamin D | 5 | 50 |
| Vitamin E | 15 | 1000 |
| Vitamin K | 0.12 | ND |
| Calcium | 1000 | 2500 |
| Chromium | 0.035 | ND |
| Copper | 0.9 | 10 |
| Fluoride | 4 | 10 |
| Iodine | 0.15 | 1.1 |
| Iron | 8 | 45 |
| Magnesium | 320 | 350 |
| Manganese | 2.3 | 11 |
| Molybdenum | 0.045 | 2 |
| Phosphorus | 700 | 4000 |
| Selenium | 0.055 | 0.4 |
| Vanadium | ND | 1.8 |
| Zinc | 11 | 40 |

Example 17

Typical RDA/UL Percentages of Final Formulation
(5 Drops)

| Ingredients | Base amount (g) | Diluted Amounts Per Gallon (g) | Amount in 5 drops (g) | US Dietary Guidelines (For Men 25-50 years old) (g) | | Percentage Difference between Dosage and the US Dietary Guidelines |
|---|---|---|---|---|---|---|
| Magnesium Chloride | 1.3800 | 5.39E−03 | 2.77E−07 | 0.35 | RDA | 0.00007920% |
| Sodium Chloride | 2.0700 | 8.09E−03 | 4.16E−07 | 2.4 | RDA | 0.00001733% |
| Potassium Chloride | 2.0700 | 8.09E−03 | 4.16E−07 | 4 | DV | 0.00001040% |
| Calcium Chloride | 1.3800 | 5.39E−03 | 2.77E−07 | 1.2 | RDA | 0.00002310% |
| Ascorbic Acid (ester C) | 11.5000 | 4.49E−02 | 2.31E−06 | 2 | UL | 0.00011551% |
| Caffeine | 1.0925 | 4.27E−03 | 2.19E−07 | 0.24 | | 0.00009144% |
| Niacin | 0.2300 | 8.98E−04 | 4.62E−08 | 0.035 | UL | 0.00013201% |
| Potassium Benzoate | 1.0350 | 4.04E−03 | 2.08E−07 | 4 | DV | 0.00000520% |
| Chromium Picolinate | 0.0043 | 1.68E−05 | 8.64E−10 | 0.00012 | DV | 0.00071999% |
| Chromium Polynicolinate | 0.0043 | 1.68E−05 | 8.64E−10 | 0.00012 | DV | 0.00071999% |
| Coenzyme Q10 | 0.7188 | 2.81E−03 | 1.44E−07 | N/A | | |
| L-Glutamine | 5.7500 | 2.25E−02 | 1.16E−06 | N/A | | |
| Potassium Sorbate | 2.3000 | 8.98E−03 | 4.62E−07 | 4 | DV | 0.00001155% |
| Vitamin A | 0.2371 | 9.26E−04 | 4.76E−08 | 2 | | 0.00000238% |
| Vitamin B1 | 0.0041 | 1.62E−05 | 8.33E−10 | 0.0011 | RDA | 0.00007569% |
| Vitamin B2 | 0.0031 | 1.22E−05 | 6.29E−10 | 0.0013 | RDA | 0.00004837% |
| Vitamin B3 | 0.0399 | 1.56E−04 | 8.02E−09 | 0.035 | UL | 0.00002292% |
| Vitamin B6 | 0.0399 | 1.56E−04 | 8.02E−09 | 0.1 | UL | 0.00000802% |
| Vitamin B12 | 0.0000 | 4.68E−08 | 2.41E−12 | 0.0000024 | RDA | 0.00010027% |
| Vitamin C | 0.1198 | 4.68E−04 | 2.41E−08 | 2 | UL | 0.00000120% |
| Vitamin D3 | 0.0190 | 7.41E−05 | 3.81E−09 | 0.00005 | UL | 0.00762078% |
| Vitamin E | 0.0014 | 5.40E−06 | 2.78E−10 | 1 | UL | 0.00000003% |
| Vitamin H | 0.0004 | 1.40E−06 | 7.22E−11 | 0.00003 | AI | 0.00024064% |
| Folic Acid | 0.0004 | 1.50E−06 | 7.70E−11 | 0.001 | RDA | 0.00000770% |
| Copper | 0.0018 | 6.86E−06 | 3.53E−10 | 0.002 | DV | 0.00001765% |
| Iron | 0.0153 | 5.96E−05 | 3.06E−09 | 0.01 | RDA | 0.00003064% |
| Potassium Iodide | 0.0001 | 5.12E−07 | 2.64E−11 | 4 | DV | 0.00000000% |
| Calcium Carbonate | 0.0799 | 3.12E−04 | 1.60E−08 | 1.2 | RDA | 0.00000134% |
| Zinc | 0.0129 | 5.02E−05 | 2.58E−09 | 0.015 | RDA | 0.00001722% |

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

What is claimed is:

1. A dietary supplement composition comprising at least two of the following in an amount equivalent to 5 drops in a liquid:
   about $2.77 \times 10^{-7}$ g magnesium;
   about $4.16 \times 10^{-7}$ g sodium;
   about $1.09 \times 10^{-6}$ g potassium;
   about $2.93 \times 10^{-7}$ g calcium;
   about $2.31 \times 10^{-6}$ g asorbic acid;
   about $2.19 \times 10^{-7}$ g caffeine;
   about $4.62 \times 10^{-8}$ g niacin;
   about $1.73 \times 10^{-9}$ g chromium;
   about $1.44 \times 10^{-7}$ g coenzyme Q-10;
   about $1.16 \times 10^{-6}$ g L-glutamine
   about $4.76 \times 10^{-8}$ g vitamin A;
   about $8.33 \times 10^{-10}$ g vitamin B1;
   about $6.29 \times 10^{-10}$ g vitamin B2;
   about $8.02 \times 10^{-9}$ g vitamin B3;
   about $8.02 \times 10^{-9}$ g vitamin B6;
   about $2.41 \times 10^{-12}$ g vitamin B12;
   about $2.41 \times 10^{-8}$ g vitamin C;
   about $3.81 \times 10^{-9}$ g vitamin D3;
   about $2.78 \times 10^{-10}$ g vitamin E;
   about $7.22 \times 10^{-11}$ g vitamin H;
   about $7.7 \times 10^{-11}$ g folic acid;
   about $3.53 \times 10^{-10}$ g copper;
   about $3.06 \times 10^{-9}$ g iron; or
   about $2.58 \times 10^{-9}$ g zinc,
   in one dose of the dietary supplement composition
   wherein the dietary supplement composition is configured in an oral strip, sublingual liquid or spray that substantially avoids first pass metabolism.

* * * * *